United States Patent
Bernhardt et al.

(10) Patent No.: US 10,919,848 B2
(45) Date of Patent: Feb. 16, 2021

(54) PROCESS FOR PREPARING METHIONINE

(71) Applicant: Evonik Operations GmbH, Essen (DE)

(72) Inventors: Sebastian Bernhardt, Aschaffenburg (DE); Martin Körfer, Kahl (DE); Stefan Reichert, Frankfurt (DE); Hans-Joachim Hasselbach, Gelnhausen (DE); Bernd Drapal, Alzenau (DE); Rainer Peter, Krombach (DE); Christian Kaiser, Waldaschaff (DE); Benny Hartono, Singapur (SG); Harald Jakob, Hasselroth (DE)

(73) Assignee: Evonik Operations GmbH, Essen (DE)

( * ) Notice: Subject to any disclaimer, the term of this patent is extended or adjusted under 35 U.S.C. 154(b) by 0 days.

(21) Appl. No.: 16/605,075

(22) PCT Filed: May 8, 2018

(86) PCT No.: PCT/EP2018/061799
§ 371 (c)(1),
(2) Date: Oct. 14, 2019

(87) PCT Pub. No.: WO2018/210615
PCT Pub. Date: Nov. 22, 2018

(65) Prior Publication Data
US 2020/0039928 A1  Feb. 6, 2020

(30) Foreign Application Priority Data

May 15, 2017 (EP) .................................. 17171060
Jul. 21, 2017 (EP) .................................. 17182515

(51) Int. Cl.
*C07C 319/20* (2006.01)
*C07C 319/28* (2006.01)
(Continued)

(52) U.S. Cl.
CPC ............ *C07C 319/20* (2013.01); *C05C 11/00* (2013.01); *C05D 1/00* (2013.01); *C05D 9/00* (2013.01);
(Continued)

(58) Field of Classification Search
CPC ... C07C 323/58; C07C 319/20; C07C 319/28; C05D 9/00
See application file for complete search history.

(56) References Cited

U.S. PATENT DOCUMENTS 4,259,525 A  3/1981  Schaaf
4,272,631 A  6/1981  Schaaf et al.
(Continued)

FOREIGN PATENT DOCUMENTS

WO  2013/030068  3/2013
WO  2016/170252  10/2016

OTHER PUBLICATIONS

International Search Report dated Jul. 10, 2018 in PCT/EP2018/061799.
(Continued)

*Primary Examiner* — Yate' K Cutliff
(74) *Attorney, Agent, or Firm* — Grüneberg and Myers PLLC

(57) ABSTRACT

A process for preparing methionine includes the alkaline hydrolysis of 5-(2-methylmercaptoethyl)-hydantoin (methionine hydantoin) in an aqueous process solution containing alkali metal hydroxide and/or alkali metal carbonate and/or alkali metal hydrogencarbonate. The alkali metal cations in the process solution are potassium and sodium having a K/Na molar ratio range from 99/1 to 20/80.

12 Claims, 3 Drawing Sheets

(51) Int. Cl.
    *C07C 323/58*     (2006.01)
    *C05C 11/00*     (2006.01)
    *C05D 1/00*     (2006.01)
    *C05D 9/00*     (2006.01)
    *C05F 11/00*     (2006.01)

(52) U.S. Cl.
    CPC ............ *C05F 11/00* (2013.01); *C07C 319/28* (2013.01); *C07C 323/58* (2013.01)

(56) References Cited

U.S. PATENT DOCUMENTS

| | | | |
|---|---|---|---|
| 5,770,769 A | | 6/1998 | Geiger et al. |
| 6,126,972 A | * | 10/2000 | Korfer ................. C07C 319/20 426/2 |
| 9,023,284 B2 | | 3/2015 | Hasselbach et al. |
| 9,403,764 B2 | | 8/2016 | Hasselbach et al. |
| 2013/0231501 A1 | | 9/2013 | Hasselbach et al. |
| 2015/0175535 A1 | | 6/2015 | Hasselbach et al. |
| 2018/0111899 A1 | | 4/2018 | Capelle et al. |

OTHER PUBLICATIONS

Written Opinion dated Jul. 10, 2018 in PCT/EP2018/061799.
P.P. Fedotev., Z. Phys. Chem. 49, 1904, 168, pp. 162-188.
Fuchs et al., Ind. Eng. Chem. Res. 2006, 45, 6578-6584.
Gmelin, Gmelins Handbuch, 22, 1938, pp. 856-864.
Mitchell et al., Journal of Plant Nutrition, 17(12), 2119-2134 (1994).
Subbarao et al., Critical Reviews in Plant Sciences, 22(5): 391-416 (2003).
A. Seidell, Solubilities—Inorganic and Metal-Organic Compounds, K—Z: A Compilation of Solubility Data from the Periodical Literature, vol. II, Fourth Edition, 1965 (3 pages).
G. Takahashi, Bull. Imp. Seric. Stn. Tokyo 29, 1927, 165.
Trypuć et al., J. Chem. Eng. Data 1998, 43, 201-204.

\* cited by examiner

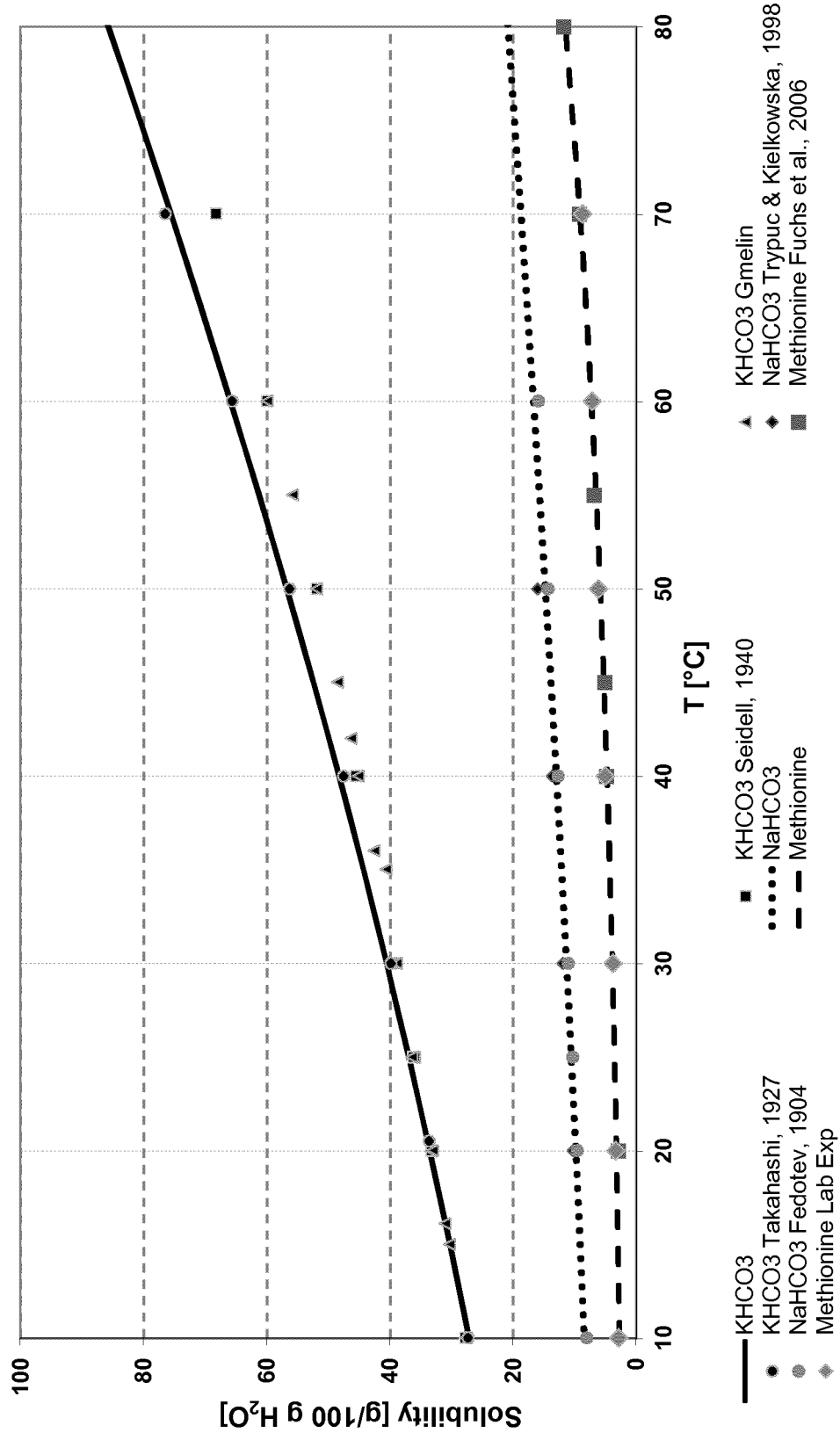
Figure 2: Solubility curves of $KHCO_3$, $NaHCO_3$ and methionine in water

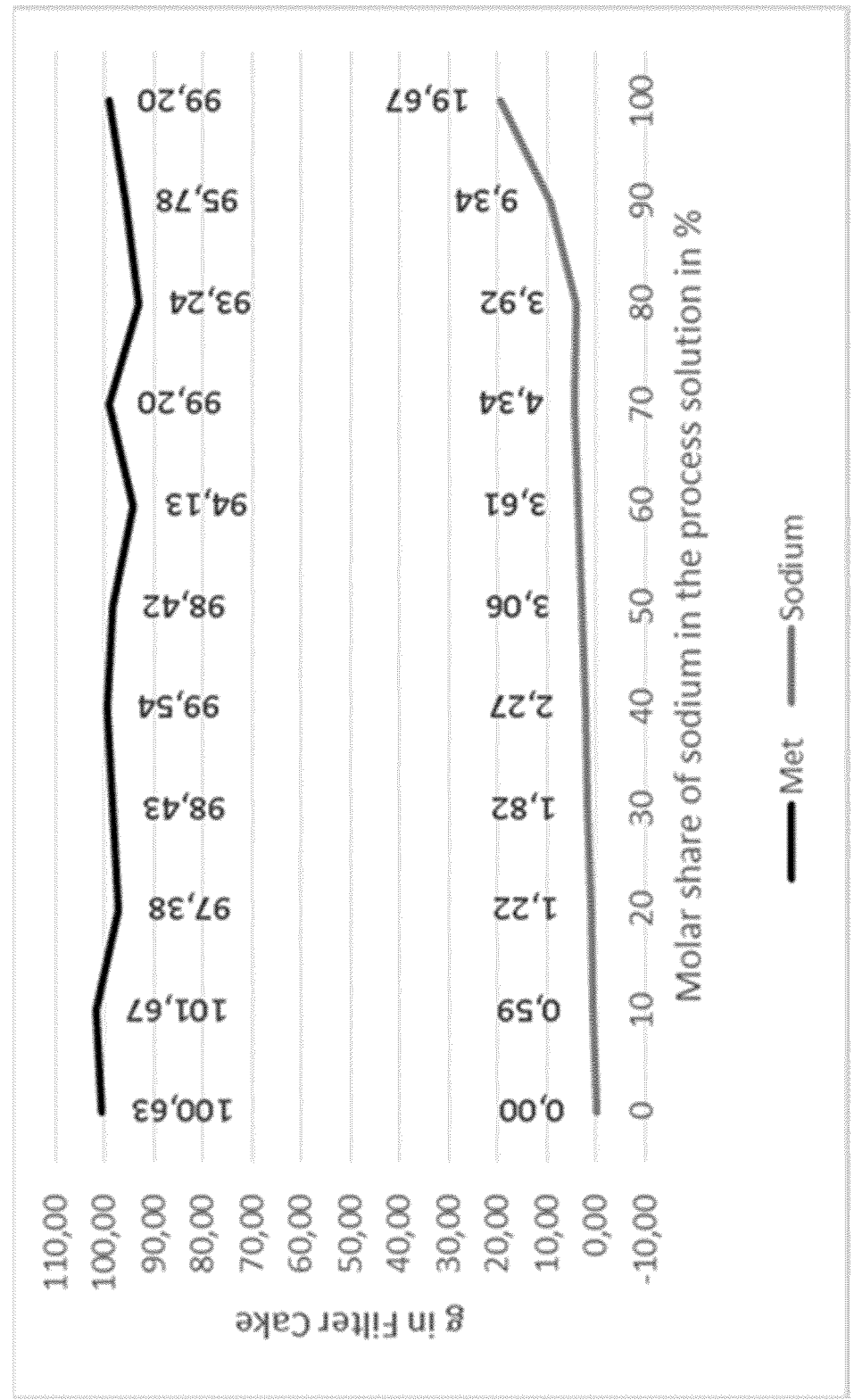
Figure 3: Composition of the raw filter cake for different molar ratios K/Na in the process solution

PROCESS FOR PREPARING METHIONINE

This application is a National Stage entry under § 371 of International Application No. PCT/EP2018/061799, filed on May 8, 2018, and which claims the benefit of European Application No. 17171060.1, filed on May 15, 2017, and European Application No. 17182515.1, filed on Jul. 21, 2017.

The present invention relates to a process for preparing methionine, comprising the alkaline hydrolysis of 5-(2-methylmercaptoethyl)-hydantoin (methionine hydantoin) in an aqueous process solution comprising alkali metal hydroxide and/or alkali metal carbonate and/or alkali metal hydrogencarbonate wherein the alkali metal cations in the process solution are potassium and sodium having a K/Na molar ratio range from 99/1 to 20/80.

The amino acid methionine is currently industrially produced worldwide in large amounts and is of considerable commercial importance. Methionine is employed in many fields, such as pharmaceutical, health and fitness products, but particularly as feedstuff additive in many feedstuffs for various livestock.

On an industrial scale, methionine is produced chemically via the Bucherer-Bergs reaction, which is a variant of the Strecker synthesis. Here, the starting substances 3-methylmercaptopropanal (prepared from 2-propenal and methylmercaptan), hydrocyanic acid (hydrogen cyanide), ammonia and carbon dioxide are reacted to give 5-(2-methylmercaptoethyl)hydantoin (methionine hydantoin) and this is subsequently hydrolysed by alkali with potassium carbonate and potassium hydrogen carbonate to give potassium methioninate. Methionine is finally liberated from its potassium salt by treatment with carbon dioxide ("carbonation reaction"), which may be filtered off as a precipitate from the mother liquor containing potassium carbonate and potassium hydrogen carbonate (U.S. Pat. No. 5,770,769). The precipitated methionine is then recrystallized from an aqueous solution, filtered off and dried. The methionine so obtained has a purity greater than 99% and a potassium content of less than 0.5%.

U.S. Pat. No. 4,272,631 demonstrates that mixtures of alkali metal and alkaline earth metal hydroxides may be used to saponify methionine hydantoin. However, in these processes the alkaline earth metal ions first have to be separated during liberation of methionine, so that maximum yields of only 80.5% are obtained. U.S. Pat. No. 4,272,631 does not disclose the use of mixtures of alkali metal hydroxides for the saponification of methionine hydantoin.

The ammonia, potassium carbonate and potassium hydrogen carbonate reagents and also carbon dioxide are generally recycled in industrial methionine production. However, it is necessary to continuously exchange a part of the aqueous process solution of this hydantoin hydrolysis circulation for fresh potassium hydroxide, essentially to remove ("purge") inactivated potassium salt from the circulation in the form of potassium formate. Potassium formate forms from the residues of hydrogen cyanide being present in the methionine hydantoin solution and alkaline potassium salts from the hydantoin hydrolysis (WO2013030068A2). A further by-product of the methionine synthesis is the dipeptide methionylmethionine (EP 1 564 208 A1). In general, the excessive enrichment of by-products in the hydantoin hydrolysis circulation must be avoided since otherwise disruptions in crystal formation occur downstream. A scheme of the hydantoin hydrolysis circulation is shown in FIG. 1.

A typical process solution recycled to the hydantoin hydrolysis circulation comprises approximately 10 to 16% by weight potassium, 5 to 10% by weight methionine, 3 to 5% by weight methionylmethionine, 0.5 to 2.0% by weight formate, and 0.2 to 0.3% by weight acetate.

Methionate and potassium may be partially recovered from the purge stream by precipitation with carbon dioxide in form of methionine and potassium carbonate, respectively, filtered off and fed back to the process solution. However, there is still a considerable loss of the relatively expensive potassium salts. The final purge solution comprises approximately 2 to 6% by weight methionine, 4 to 8% by weight methionylmethionine and 6 to 14% by weight potassium in the form of potassium salts, 1 to 1.7% by weight formate, and 0.3 to 0.5% by weight acetate.

With the aim to recycle the excess of sodium carbonate Capelle and Rey (WO 2016/170252 A1) propose a method for producing methionine by alkaline hydrolysis of methionine hydantoin in aqueous phase, eliminating ammonia and carbon dioxide from the hydrolysis medium, and neutralising the methionine sodium salt obtained, wherein after the elimination of ammonia and carbon dioxide the reaction medium is concentrated in order to precipitate sodium carbonate which is filtered off and recycled for alkaline hydrolysis in the presence of sodium hydroxide and sodium carbonate. However, in this method the neutralisation of the methionine sodium salt is achieved with sulphurous acid still leading to large amounts of sodium sulphate as side product which has to be removed from the process.

In the carbonation reaction, i.e. reaction of the alkali metal salt of methionine with carbon dioxide to form methionine and alkali metal hydrogencarbonate (FIG. 1), methionine is precipitated and removed from the process solution. However, due to the low difference in the solubility of sodium hydrogencarbonate and methionine (FIG. 2), large quantities of sodium hydrogencarbonate are co-precipitated with methionine in case that sodium salt of methionine is used in this reaction. Therefore, in the carbonisation reaction the potassium salt of methionine is used, meaning that potassium hydroxide usually is added to the hydantoin hydrolysis circulation process.

From U.S. Pat. Nos. 4,259,525 and 5,770,769 it is also known that when sodium salts or hydroxides instead of potassium salts or hydroxides are employed in the hydrolysis of the methionine hydantoin, the methionine precipitated with carbon dioxide tends to contain high levels of sodium due to a poor solubility of sodium carbonate which precipitates with the product.

The object of the present invention is to provide a process for preparing methionine, comprising the alkaline hydrolysis of 5-(2-methylmercaptoethyl)-hydantoin (methionine hydantoin) in an aqueous process solution comprising potassium hydroxide and/or carbonate and/or hydrogencarbonate to form methionine potassium salt, precipitation of methionine by means of carbon dioxide, separation of the precipitated methionine from the process solution, concentration of the process solution and recycling of the process solution to the alkaline hydrolysis of methionine hydantoin, wherein the potassium cations in the process solution are partly replaced by sodium cations in order to avoid losses of the relatively expensive potassium salts in the purge solution stream.

It was found that in the process solution resulting from the hydantoin hydrolysis reaction a large part of potassium can be replaced by sodium without the undesired co-precipitation of sodium hydrogencarbonate in the carbonation reaction.

This object is achieved by a process for preparing methionine, comprising the alkaline hydrolysis of 5-(2-methylmercaptoethyl)-hydantoin (methionine hydantoin) in an aqueous process solution comprising alkali metal hydroxide and/or alkali metal carbonate and/or alkali metal hydrogencarbonate to form methionine alkali metal salt, precipitation of methionine by means of carbon dioxide, separation of the precipitated methionine from the process solution, concentration of the process solution and recycling of the process solution in the alkaline hydrolysis of methionine hydantoin once more forwarded to the process solution, wherein the alkali metal cations in the process solution are potassium and sodium having a K/Na molar ratio range from 99/1 to 20/80 resulting in potassium concentrations ranging from 13.9% by weight to 1.2% by weight and sodium concentrations ranging from 0.04% by weight to 6.6% by weight.

During the concentration step the process solution is re-concentrated to its typical starting concentrations of the hydantoin hydrolysis circulation, i.e. comprising approximately 5 to 16% by weight alkali metal, 5 to 8% by weight methionine, 3 to 5% by weight methionylmethionine, 0.7 to 1.1% by weight formate, and 0.2 to 0.3% by weight acetate.

In the process according to the present invention the K/Na molar ratio in the process solution preferably ranges from 90/10 to 20/80 resulting in potassium concentrations ranging from 12.6% by weight to 1.2% by weight and sodium concentrations ranging from 0.35% by weight to 6.6% by weight. Ideally, the K/Na molar ratio in the process solution ranges from 70/30 to 50/50 resulting in potassium concentrations ranging from 9.8% by weight to 3% by weight and sodium concentrations ranging from 1.06% by weight to 4.1% by weight.

In the process according to the present invention the precipitated methionine is then recrystallized from an aqueous solution, filtered off and dried. The methionine so obtained has a purity greater than 99% and a potassium content lower than 0.3% and a sodium content lower than 0.1%, in particular the potassium content in the crystalline methionine ranges from 0.05-0.3% and the sodium content ranges from 0.01-0.1%.

In the process according to the present invention a part of the process solution, the so called "purge solution", may continuously be removed from the process and exchanged by fresh alkali metal hydroxide solution.

The purge solution removed from the process comprises 2 to 6% by weight methionine, 4 to 8% by weight methionylmethionine, 1 to 1.7% by weight formate, 0.3 to 0.5% by weight acetate and 6 to 14% by weight alkali metal in the form of potassium and sodium salts, potassium and sodium having a K/Na molar ratio range from 99/1 to 20/80 resulting in potassium concentrations ranging from 13.9% by weight to 1.2% by weight and sodium concentrations ranging from 0.04% by weight to 6.6% by weight.

The process according to the present invention may also lead to purge solutions having a K/Na molar ratio range from 90/10 to 20/80 resulting in potassium concentrations ranging from 12.6% by weight to 1.2% by weight and sodium concentrations ranging from 0.35% by weight to 6.6% by weight.

The process according to the present invention may also lead to purge solutions having a K/Na molar ratio range from 70/30 to 50/50 resulting in potassium concentrations ranging from 9.8% by weight to 3% by weight and sodium concentrations ranging from 1.06% by weight to 4.1% by weight.

Due to the potassium, nitrogen, sulphur and sodium content, the purge solution is suitable as a liquid fertilizer (C. C. Mitchel and A. E. Hiltbold, Journal of Plant Nutrition, 17(12), 2119-2134, 1994). Furthermore, sodium is considered being a functional nutrient for plants, i.e. an element which promotes maximal biomass yield and/or which reduces the requirement (critical level) of an essential element (Subbarao et al., Critical Reviews in Plant Sciences, 22(5):391-416 (2003)).

The purge solution may comprise 2 to 6% by weight methionine, 4 to 8% by weight methionylmethionine, 1 to 1.7% by weight formate, 0.3 to 0.5% by weight acetate and 13.9% by weight to 1.2% by weight potassium in form of potassium salts and 0.04% by weight to 6.6% by weight sodium in form of sodium salts. The purge solution may also have potassium concentrations ranging from 12.6% by weight to 1.2% by weight and sodium concentrations ranging from 0.35% by weight to 6.6% by weight. The purge solution according may alternatively have potassium concentrations ranging from 9.8% by weight to 3% by weight and sodium concentrations ranging from 1.06% by weight to 4.1% by weight.

Due to its composition, the purge solution may be used as fertilizer or fertilizer additive.

BRIEF DESCRIPTION OF THE FIGURES

FIG. 2 shows the solubility curves of $KHCO_3$, $NaHCO_3$ and methionine in water. The measured values stem from the following sources.

Figure 1:
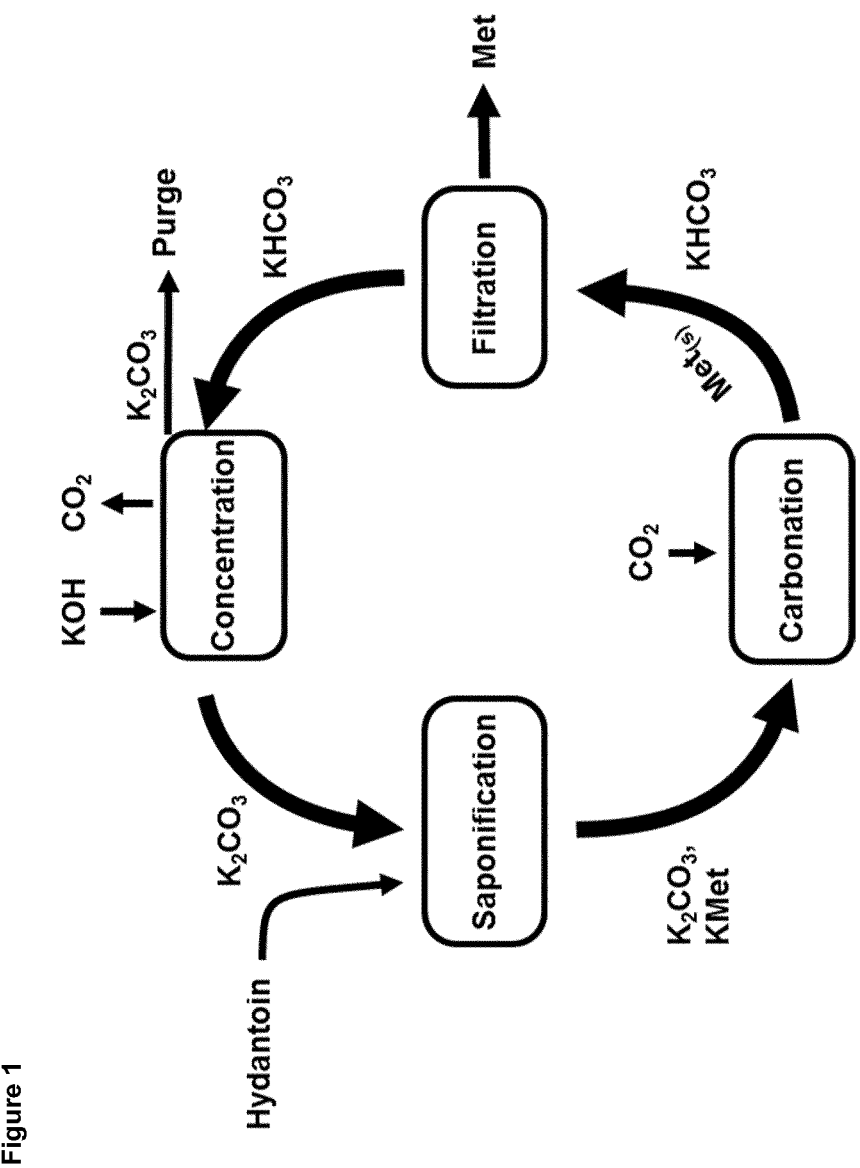
FIG. 1 shows a scheme of the hydantoin hydrolysis circulation.

Solubility of $KHCO_3$:
Seidell, 1940: Seidel, A.; Solubility Data Ser., 1940.
Gmelin: Gmelins Handbuch, 22, 1938.
Takahashi, 1927: Takahashi, G.; Bull. Imp. Seric. Stn. Tokyo 29, 1927, 165.

Solubility of $NaHCO_3$:
Trypuc & Kielkowska, 1998: Trypuc, M.; Kielkowska, U.; J. Chem. Eng. Data 43 (2), 1998, 201-204.
Fedotev, 1904: Fedotev, P. P., Z. Phys. Chem. 49, 1904, 168.

Solubility of Methionine:
Fuchs et al., 2006: Fuchs et al., 2006, Ind. Eng. Chem. Res., 45, 6578-6584.
Lab Exp: Results of own laboratory experiments (in accordance to Fuchs et al., 2006).

FIG. 3 shows the composition of the raw filter cake for different molar ratios K/Na in the process solution (Example 1).

EXPERIMENTAL PART

In the carbonation reaction the potassium salt of methionine (K-Met) accompanied by 0.5 equivalents of potassium carbonate is reacted with $CO_2$. $KHCO_3$ is formed and methionine (H-Met) is precipitated (Equations 1 and 2).

K-Met+$CO_2$+$H_2O$->H-Met(s)+$KHCO_3$ (Equation 1)

$K_2CO_3$+$CO_2$+$H_2O$->$2KHCO_3$ (Equation 2)

Due to the significantly lower solubility of $NaHCO_3$ compared to $KHCO_3$ (FIG. 2) the molar ratio of K/Na has to be carefully tuned in order to avoid undesired precipitation of $NaHCO_3$ crystals in the carbonation reactor.

Thus, a series of experiments was carried out in the laboratory to investigate the carbonation reaction with synthetic process solutions for different molar ratios K/Na. The overall alkaline concentration (sum parameter of K and Na) is maintained constant meaning that for a molar ratio K/Na=70/30 compared to K/Na=100/0 the potassium concentration is lowered by 30% and replaced equimolar by sodium. The results of this study are summarized in FIG. 3.

The methionine content in the filter cake can be considered being constant for molar ratios K/Na 100/0 to 0/100. The Na-content in the filter cake is slightly increasing for molar ratios K/Na 100/0 to 20/80 up to 3.92 g which can be explained by process solution being attached to and incorporated into the filter cake. However, for molar ratios K/Na 10/90 and 0/100 significantly higher Na content 9.34-19.67 g) was observed in the filter cake indicating that $NaHCO_3$ is also partially precipitated.

Thus, it is possible to run the carbonation reaction up to molar ratios K/Na 20/80 without co-precipitations of sodium hydrogencarbonate.

Example 1

Experimental procedure for the preparation of a process solution with a molar ratio K/Na of 90/10

A 1000 ml beaker was placed in an ice bath and KOH (40% in water, 354.2 g, 2.53 mol), NaOH (40% in water, 11.2 g, 0.28 mol), D,L-methionine (159.7 g, 1.07 mol), DL-methionyl-DL-methionine (29.9 g, 0.11 mol) and formic acid (50% in water, 41.4 g, 0.45 mol) were dissolved in 200 ml DI-water and stirred for 45 min. The solution was then warmed to 20° C., transferred to a 1000 ml volumetric flask and filled up with DI-water to 1000 ml total volume.

1100 g of the solution was then transferred to a 2 l Büchi laboratory autoclave and 0.32 g of Defoamer EG2007 were added. Cooling of the autoclave to 30° C. was realized via cooling jacket and cryostat. Mechanical stirring was initiated and the autoclave was pressurized with $CO_2$ gas to 2 barg. The $CO_2$ gas feedstream was adjusted to maintain 2 barg until pH 8 was reached and temperature was maintained at 30° C. Pressure was released from the autoclave and the suspension was transferred to a vacuum filter frit and sucked dry for 15 min at 940 mbar absolute pressure. The filtrate was collected in a 100 ml glass bottle and diluted with DI-water to avoid precipitation of solids afterwards and balanced subsequently. The filter cake was transferred to 3000 ml beaker via spatula and residual solids in the frit were rinsed into the beaker via DI-water. Additional DI-water was added until the solids have been dissolved. The solution was then transferred to a 3 l glass bottle and balanced. Moreover, the residual solids in the autoclave were also rinsed with DI-water collected in a glass bottle as so-called "Holdup" and balanced.

The synthetic process solution, the filter cake dissolved in DI-water, the filtrate and the "Holdup" were analysed for their K and Na content via IPC-OES, Met-& Met-Met via HPLC and formate via ion chromatography and the results are summarized in Table 1.

The invention claimed is:
1. A process for preparing methionine, comprising:
  alkaline hydrolyzing of 5-(2-methylmercaptoethyl)-hydantoin in an aqueous process solution, comprising alkali metal hydroxide, alkali metal carbonate, and/or alkali metal hydrogen carbonate to form methionine alkali metal salt,
  treating the methionine alkali metal salt with carbon dioxide to yield precipitated methionine,
  separating the precipitated methionine from the aqueous process solution which was treated with carbon dioxide,
  concentrating an aqueous process solution from which methionine has been removed, and
  recycling of a concentrated aqueous process solution in the alkaline hydrolyzing of 5-(2-methylmercapto-ethyl)-hydantoin to the aqueous process solution,
  wherein alkali metal cations in the aqueous process solution of alkaline hydrolyzing are potassium and sodium, having a K/Na molar ratio range from 99/1 to 20/80.

2. The process as claimed in claim 1, wherein the K/Na molar ratio in the aqueous process solution ranges from 90/10 to 20/80.

3. The process as claimed in claim 1, wherein the K/Na molar ratio in the aqueous process solution ranges from 70/30 to 50/50.

4. The process as claimed in claim 1, wherein the precipitated methionine is recrystallized from the aqueous process solution, wherein the precipitated methionine is filtered off and dried to yield crystalline methionine, and wherein the crystalline methionine so obtained has a purity greater than 99%, a potassium content lower than 0.3%, and a sodium content lower than 0.1%.

5. The process as claimed in claim 4, wherein the potassium content in the crystalline methionine ranges from 0.05-0.3% and the sodium content ranges from 0.01-0.1%.

6. The process as claimed in claim 1 further comprising continuously removing a purge solution from the process and exchanging the purge solution with fresh alkali metal hydroxide solution.

7. The process as claimed in claim 1, wherein, within the aqueous process solution, potassium concentration ranges from 13.9% by weight to 1.2% by weight and sodium concentration ranges from 0.04% by weight to 6.6% by weight.

8. The process as claimed in claim 6, wherein the purge solution comprises:
  2 to 6% by weight of methionine,
  4 to 8% by weight of methionyl methionine,
  1 to 1.7% by weight of formate,
  0.3 to 0.5% by weight of acetate, and

TABLE 1

Carbonation reaction of synthetic process solution with molar ratio K/Na of 90/10.

|  | Quantity g | % Met | g Met | % Met-Met | g Met-Met | % K | g K | % Na | g Na |
|---|---|---|---|---|---|---|---|---|---|
| Start | 1099.85 | 14.14 | 155.52 | 2.58 | 28.38 | 8.2 | 90.19 | 0.59 | 6.489 |
| Filtrate | 1001.1 | 4.14 | 41.45 | 2.25 | 22.52 | 7.1 | 71.08 | 0.51 | 5.106 |
| Cake | 2930.1 | 3.47 | 101.67 | 0.120 | 3.52 | 0.3 | 8.79 | 0.02 | 0.586 |
| Holdup | 498.8 | 1.88 | 9.38 | 0.25 | 1.25 | 0.75 | 3.74 | 0.05 | 0.249 |
| mF + C + H [g] |  |  | 152.50 |  | 27.29 |  | 83.61 |  | 5.94 |
| Accuracy [%] |  |  | 98.06 |  | 96.16 |  | 92.71 |  | 91.55 |

6 to 14% by weight of alkali metal in the form of potassium and sodium salts, wherein the purge solution has a K/Na molar ratio range from 99/1 to 20/80.

9. The process as claimed in claim 8, wherein, within the purge solution, potassium concentration ranges from 13.9% by weight to 1.2% by weight and sodium concentration ranges from 0.04% by weight to 6.6% by weight.

10. The process as claimed in claim 9, wherein, within the purge solution, potassium concentration ranges from 9.8% by weight to 3% by weight and sodium concentration ranges from 1.06% by weight to 4.1% by weight.

11. A fertilizer or fertilizer additive, comprising:

the purge solution obtained according to the process of claim 6.

12. The process as claimed in claim 1, further comprising:

reacting 3-methylmercaptopropanal, hydrocyanic acid, ammonia, and carbon dioxide, thereby obtaining the 5-(2-methylmercaptoethyl)hydantoin.

* * * * *